(12) United States Patent
Park (10) Patent No.: US 11,453,857 B2
(45) Date of Patent: Sep. 27, 2022

(54) LACTOBACILLUS FERMENTUM LM1016 STRAIN (KCCM12468P)

(71) Applicants: Genome And Company, Gyeonggi-do (KR); Lactomason Co., Ltd., Gyeongsangnam-do (KR)

(72) Inventor: Han Soo Park, Seoul (KR)

(73) Assignees: Genome and Company, Gyeonggi-do (KR); Lactomason Co., Ltd., Gyeongsangnam-do (KR)

(*) Notice: Subject to any disclaimer, the term of this patent is extended or adjusted under 35 U.S.C. 154(b) by 71 days.

(21) Appl. No.: 17/041,740

(22) PCT Filed: Mar. 25, 2019

(86) PCT No.: PCT/KR2019/003462
§ 371 (c)(1),
(2) Date: Sep. 25, 2020

(87) PCT Pub. No.: WO2019/190146
PCT Pub. Date: Oct. 3, 2019

(65) Prior Publication Data
US 2021/0115392 A1 Apr. 22, 2021

(30) Foreign Application Priority Data

Mar. 26, 2018 (KR) .................. 10-2018-0034612

(51) Int. Cl.
| | |
|---|---|
| *A61K 35/747* | (2015.01) |
| *C12N 1/20* | (2006.01) |
| *A23K 50/50* | (2016.01) |
| *A23K 10/18* | (2016.01) |
| *A23L 33/135* | (2016.01) |
| *A61P 1/16* | (2006.01) |
| *A61P 9/00* | (2006.01) |
| *A61P 3/06* | (2006.01) |
| *A61P 3/10* | (2006.01) |
| *A61P 29/00* | (2006.01) |

(52) U.S. Cl.
CPC ............... *C12N 1/20* (2013.01); *A23K 10/18* (2016.05); *A23K 50/50* (2016.05); *A23L 33/135* (2016.08); *A61K 35/747* (2013.01); *A61P 1/16* (2018.01); *A61P 3/06* (2018.01); *A61P 3/10* (2018.01); *A61P 9/00* (2018.01); *A61P 29/00* (2018.01); *A23V 2002/00* (2013.01); *A23Y 2220/35* (2013.01)

(58) Field of Classification Search
None
See application file for complete search history.

(56) References Cited

FOREIGN PATENT DOCUMENTS

| | | |
|---|---|---|
| JP | 2016511742 A | 4/2016 |
| KR | 20050010451 A | 1/2005 |
| KR | 20150118084 A | 10/2015 |
| KR | 20160098955 A | 8/2016 |
| KR | 20180011490 A | 2/2018 |

OTHER PUBLICATIONS

Yoon, Y. et al. Lactobacillus fermentum Promotes Adipose Tissue Oxidative Phosphorylation to Protect Against Diet Induced Obesity. Experimental & Molecular Medicine 52:1574-1586, 2020. (Year: 2020).*
Aronson, D. , et al., "Obesity is the major determinant of elevated C-reactive protein in subjects with the metabolic syndrome", International Journal of Obesity (2004) 28, 674-679.
Ballantyne, Christie M., et al., "Lipoprotein-Associated Phospholipase A2, High-Sensitivity C-Reactive Protein, and Risk for Incident Coronary Heart Disease in Middle-Aged Men and Women in the Atherosclerosis Risk in Communities (ARIC) Study", Circulation. 2004;109:837-842.
Boekholdt, S. Matthijs, et al., "C-reactive protein levels and coronary artery disease incidence and mortality in apparently healthy men and women: The EPIC-Norfolk prospective population study 1993-2003", Atherosclerosis 187 (2006) 415-422.
Engelsen, Corine Den, et al., "High-sensitivity C-reactive protein to detect metabolic syndrome in a centrally obese population: a cross-sectional analysis", Cardiovascular Diabetology 2012, 11:25.
Kim, Myung-Sunny , et al., "Inflammation-mediated obesity and insulin resistance as targets for nutraceuticals", Ann. N.Y. Acad. Sci. 1229 (2011) 140-146.
Koenig, Wolfgang , et al., "C-Reactive Protein Modulates Risk Prediction Based on the Framingham Score: Implications for Future Risk Assessment: Results From a Large Cohort Study in Southern Germany", Circulation. 2004;109:1349-1353.
Launay, J.-M. , "Function of the serotonin 5-hydroxytryptamine 2B receptor in pulmonary hypertension", Nature Medicine 8(10): 11129-1135, Oct. 2002.
Li, Xiuliang , et al., "Lactobacillus plantarum and Lactobacillus fermentum alone or in combination regulate intestinal flora composition and systemic immunity to alleviate obesity syndrome in high-fat diet rat", International Journal of Food Science and Technology 2018, 53, 137-146.
Mikelsaar, Marika, et al., "Lactobacillus fermentum ME-3—an antimicrobial and antioxidative probiotic", Microbial Ecology in Health and Disease. 2009; 21: 1-27.
Pai, Jennifer K., et al., "Inflammatory Markers and the Risk of Coronary Heart Disease in Men and Women", N Engl J Med 2004;351:2599-610.
Ridker, Paul M., et al., "Comparison of C-Reactive Protein and Low-Density Lipoprotein Cholesterol Levels in the Prediction of First Cardiovascular Events", N Engl J Med, vol. 347, No. 20, Nov. 14, 2002, 1557-1565.

(Continued)

*Primary Examiner* — Ralph J Gitomer
(74) *Attorney, Agent, or Firm* — Servilla Whitney LLC (57) ABSTRACT

The present disclosure relates to a novel strain of *Lactobacillus fermentum* LM1016 (KCCM12468P). The disclosed strain can be useful for treating or preventing cardiovascular diseases, obesity, fatty liver and/or diabetes. The present disclosure also relates to compositions comprising the strain. The compositions can be useful for medicines, health-functional foods, dairy products, fermented products, food additives, animal feeds, etc.

10 Claims, 10 Drawing Sheets

(56) References Cited

OTHER PUBLICATIONS

Ridker, Paul M., et al., "C-Reactive Protein and Other Markers of Inflammation in the Prediction of Cardiovascular Disease in Women", The New England Journal of Medicine, vol. 342, No. 12, 2000, 836-843.

Ridker, Paul M., et al., "Inflammation, Aspirin, and the Risk of Cardiovascular Disease in Apparently Healthy Men", The New England Journal of Medicine, vol. 336, No. 14, Apr. 3, 1997, 973-979.

Ridker, Paul M., et al., "Rosuvastatin to Prevent Vascular Events in Men and Women with Elevated C-Reactive Protein", N Engl J Med 2008;359:2195-207.

Sugiura, Tomonori, et al., "Serotonin in peripheral blood reflects oxidative stress and plays a crucial role in atherosclerosis: Novel insights toward holistic antiatherothrombotic strategy", Atherosclerosis 246 (2016) 157e160.

Tomaro-Duchesneau, Catherine, et al., "Effect of orally administered L. fermentum NCIMB 5221 on markers of metabolic syndrome: an in vivo analysis using ZDF rats", Appl Microbiol Biotechnol (2014) 98:115-126.

Westfall, Susan, et al., "Ferulic Acid Produced by Lactobacillus fermentum NCIMB 5221 Reduces Symptoms of Metabolic Syndrome in *Drosophila melanogaster*", J Microb Biochem Technol vol. 8(4): 272-284 (2016).

Xie, Ning, et al., "Effects of two Lactobacillus strains on lipid metabolism and intestinal microflora in rats fed a high-cholesterol diet", BMC Complementary and Alternative Medicine 2011, 11:53.

Yeniova, Abdullah Ozgur, et al., "High-Sensitivity C-Reactive Protein Is A Strong Predictor Of Non-Alcoholic Fatty Liver Disease", Hepato-Gastroenterology 2014; 420-423.

\* cited by examiner

Inguinal Fat

Epididymal Fat

Brown adipose tissue

HFD

Change in Tissue
(H & E staining)
X 20

ND

HFD

LM1016

LACTOBACILLUS FERMENTUM LM1016 STRAIN (KCCM12468P)

CROSS-REFERENCE TO RELATED APPLICATIONS

This application is the National Stage entry of PCT/KR2019/003462, filed on Mar. 25, 2019, which claims priority to Korean Application Serial No. 10-2018-0034612, filed Mar. 26, 2018, the entire disclosures of which are hereby incorporated by reference herein.

TECHNICAL FIELD

The present invention relates to a novel LM1016 strain of *Lactobacillus fermentum* (*Lactobacillus fermentum* LM1016). The novel strain of the present invention has an excellent effect of treating or preventing cardiovascular diseases, obesity, fatty liver and diabetes mellitus at the same time.

Specifically, the *Lactobacillus fermentum* LM1016 strain of the present invention not only reduces the level of c-reactive protein (CRP), which is an independent risk factor for cardiovascular diseases, but also has an effect of reducing the concentrations of neutral fat and cholesterol in blood at the same time. In addition, it inhibits the accumulation of body fat, thereby preventing overweight, and reduces the blood glucose concentration and the blood insulin concentration, thereby inhibiting insulin resistance and thus having an effect of preventing and treating diabetes mellitus. In addition, it inhibits the accumulation of fat in the liver tissue, thereby having an effect of inhibiting and reducing the occurrence of fatty liver.

BACKGROUND ART

Cardiovascular disease refers to a disease that occurs in the heart and main arteries, and is a disease in which bleeding occurs due to blockage, stretching, or bursting of main arteries. According to data from the Statistics Korea in 2015, the number of cardiovascular disease deaths was 28,260, which is the second cause of death in Korea and the first cause of death as a single disease. In particular, the death rate of circulatory system disease significantly increases in men over 55 years of age and women over 65 years of age.

Representative cardiovascular diseases include myocardial infarction, angina, heart failure, atrial fibrillation, stroke and the like, and the main causes may include middle-aged or older age, hypertension, hyperlipidemia, diabetes mellitus, smoking, lack of exercise, overweight and the like. Therefore, in order to prevent myocardial infarction or stroke, in the case of patients having vascular disease, diabetes mellitus or hyperlipidemia, the use of statin drugs to reduce LDL was a recent practice guideline. However, it was confirmed that more than half of patients that developed myocardial infarction or stroke had a normal LDL level.

Recent research results reveal that inflammation is an important etiology for arteriosclerosis, and in particular, it was found that C-reactive protein (CRP) is an important etiology for cardiovascular diseases such as arteriosclerosis. In addition, it is known that CRP is directly related to the process of arteriosclerosis, and thus, CRP is attracting attention as a new biomarker of cardiovascular diseases.

The results of various studies have been reported that CRP is an independent risk factor for cardiovascular disease, and it acts independently of previously identified risk factors and is directly related to cardiovascular diseases regardless of the level of LDL cholesterol, which is known as one of the most important risk factors. This hypothesis was proved through the results of a prospective large-scale clinical trial completed in 2008, and through this, rosuvastatin used in the clinical trial was approved as a drug for preventing cardiovascular diseases regardless of the LDL level in various countries including the U.S. Food and Drug Administration.

CRP inhibits the production of nitric oxide and increases the secretion of endothelin, thereby increasing adhesion molecules such as ICAM-1 and VCAM and chemotactic factors such as MCP-1, and thus reducing the function of vascular endothelial cells. In addition, CRP stimulates monocytes to move into the blood vessel wall and stimulates the secretion of inflammatory cytokines such as IL-1, IL-6, and TNF-α. CRP may opsonize low-density lipoprotein and mediate the phagocytosis of low-density lipoprotein by macrophage, and stimulate the production of tissue factor, and increase plasminogen activator inhibitor (PAI-1) to increase the formation of blood clots.

It is known that some of cardiovascular diseases often result from complications of diabetes mellitus, and 70% of diabetic patients die from cardiovascular complications, and those with diabetes mellitus have a risk of the occurrence of cardiovascular diseases up to four times higher. When the blood sugar level is high, blood vessels become narrower and eventually become clogged, leading to the occurrence of cardiovascular diseases. Therefore, managing blood sugar well is helpful in preventing cardiovascular disease as well as diabetes mellitus.

In addition, cardiovascular disease is the most important cause of death in patients with type 2 diabetes mellitus, and the occurrence of complications due to diabetes mellitus is correlated with the degree of hyperglycemia, and it is known that the occurrence of microvascular complications and macrovascular complications increase when hyperglycemia persists.

Obesity is an abnormality in energy metabolism caused by the imbalance between energy intake and energy consumption, and is consequently defined as a state of the excess accumulation of neutral fats in the fat cells. Obesity is a chronic disease that is taken as problematic all over the world, and there is no effective treatment method therefor, and it is a serious disease that is on a rising trend. Obesity, unlike other diseases, is characterized not only by a physical appearance problem but also by the accompaniment of related diseases such as metabolic disease, hypertension, diabetes mellitus, hyperlipidemia, arteriosclerosis, ischemic heart disease, fatty liver, gallstone disease and the like along with the body weight gain.

Fatty liver is caused by the accumulation of excess fat, particularly neutral fat, in the liver tissue, and it is generally diagnosed as fatty liver when fat is accumulated in an amount of more than 5% of the weight of the liver. Fatty liver is classified into alcoholic and non-alcoholic fatty liver, and non-alcoholic fatty liver occurs mainly in association with obesity, diabetes mellitus, hyperlipidemia and the like.

Those who have non-alcoholic fatty liver show a higher arterial stiffness level in 42% than those who do not have non-alcoholic fatty liver. This shows a higher risk of arterial stiffness as the degree of fatty liver is severe, and it is known that the presence or absence of fatty liver can be considered as a risk factor for cardiovascular disease.

Lactic acid bacteria play roles in breaking down fibrous and conjugated proteins into important nutrients while having symbiotic relationships with the digestive system of the human body. As such, probiotics are collectively referred to as living microorganisms that have beneficial influence on the health of a host by ameliorating the intestinal microbial environment of the host in the gastrointestinal tract of an animal including a human being.

Probiotics are known to have the ability to regulate metabolism and immunological function. Representative probiotics include a *Lactobacillus* sp. strain, a *Lactococcus* sp. strain and the like. Among them, a *Lactobacillus* sp. strain has been known to play an important role in maintaining a healthy digestive organ and intravaginal environment as a major member of a normal microbial community living in the intestine of the human body.

Cardiovascular diseases, obesity, diabetes mellitus and the like are very serious chronic diseases for modern people, and since these diseases are interrelated and require long-term drug use, there is a high concern about side effects.

Therefore, there is a very high demand for a drug or method capable of preventing or treating chronic diseases such as cardiovascular diseases, obesity, and diabetes mellitus without side effects of drugs, but until now, effective drugs and treatment methods for all these diseases have not been found.

The present inventors have conducted various studies to find an effective method capable of treating the chronic disease without side effects through probiotics. Based on the above, the present inventors completed the present invention.

PRIOR ART DOCUMENT

Non-Patent Document (Non-Patent Document 1) Ridker P M, Cushman M, Stampfer M J, Tracy R P, Hennekens C H. Inflammation, aspirin, and the risk of cardiovascular disease in apparently healthy men. N Engl J Med 1997; 336:973-9.
(Non-Patent Document 2) Ridker P M, Hennekens C H, Buring J E, Rifai N. C-reactive protein and other markers of inflammation in the prediction of cardiovascular disease in women. N Engl J Med 2000; 342:836-43.
(Non-Patent Document 3) Ridker P M, Rifai N, Rose L, Buring J E, Cook N R. Comparison of C-reactive protein and low-density lipoprotein cholesterol levels in the prediction of first cardiovascular events. N Engl J Med 2002; 347:1557-65.
(Non-Patent Document 4) Koenig W, Lowel H, Baumert J, Meisinger C. C-reactive protein modulates risk prediction based on the Framingham score: implications for future risk assessment: results from a large cohort study in southern Germany. Circulation 2004; 109:1349-53.
(Non-Patent Document 5) Pai J K, Pischon T, Ma J, et al. Inflammatory markers and the risk of coronary heart disease in men and women. N Engl J Med 2004; 351: 2599-610.
(Non-Patent Document 6) Boekholdt S M, Hack C E, Sandhu M S, et al. C-reactive protein levels and coronary artery disease incidence and mortality in apparently healthy men and women: the EPIC-Norfolk prospective population study 1993-2003. Atherosclerosis 2006; 187: 415-22.
(Non-Patent Document 7) Ballantyne C M, Hoogeveen R C, Bang H, et al. Lipoprotein-associated phospholipase A2, high-sensitivity C-reactive protein, and risk for incident coronary heart disease in middle-aged men and women in the Atherosclerosis Risk in Communities (ARIC) study. Circulation 2004; 109:837-42.
(Non-Patent Document 8) Paul M Ridker, et al. Rosuvastatin to Prevent Vascular Events in Men and Women with Elevated C-Reactive Protein. N Engl J Med 2008; 359: 2195-207.

DETAILED DESCRIPTION OF THE INVENTION

Technical Problem

The present inventors have studied intensively for the purpose of discovering a method that can effectively treat chronic diseases such as cardiovascular diseases, obesity and diabetes mellitus at the same time without side effects through probiotics. As a result, the present invention has been completed.

The present inventors have studied several probiotics and found that LM1016, a novel strain of *Lactobacillus fermentum*, reduces the levels of CRP, neutral fat and cholesterol in blood, thereby having an effect of preventing and treating cardiovascular diseases.

In addition, the present inventors further have found that LM1016 not only reduces body fat and subcutaneous fat, thereby having an effect of preventing and treating obesity, but also reduces inflammation in subcutaneous fat and reduces the levels of blood sugar, insulin and leptin, thereby having an effect on diabetes mellitus.

Solution to Problem

The present invention relates to a novel *Lactobacillus fermentum* LM1016 strain deposited with the Korean Culture Center of Microorganisms under accession number KCCM12468P.

The *Lactobacillus fermentum* LM1016 of the present invention was deposited with the Korean Culture Center of Microorganisms as KFCC11756P on Dec. 13, 2017 (domestic deposit), and the same strain was deposited with the Korean Culture Center of Microorganisms as KCCM12468P on Mar. 22, 2019 (international deposit).

The present invention relates to a composition having an effect on cardiovascular diseases, comprising the *Lactobacillus fermentum* LM1016 strain. In one embodiment, the present invention provides a method for preventing, ameliorating or treating cardiovascular diseases in a subject in need thereof, comprising administering an effective amount of a *Lactobacillus fermentum* LM1016 strain to the subject in need of preventing, ameliorating or treating cardiovascular diseases. Specifically, the *Lactobacillus fermentum* LM1016 strain of the present invention has an effect of reducing the level of CRP (C-reactive protein), neutral fat or cholesterol, which is an independent risk factor of cardiovascular diseases.

The present invention relates to a composition having an effect on cardiovascular diseases, obesity, diabetes mellitus or fatty liver disease, comprising a *Lactobacillus fermentum* LM1016 strain. In one embodiment, the present invention provides a method for preventing, ameliorating or treating cardiovascular diseases, obesity, diabetes mellitus or fatty liver disease in a subject in need thereof, comprising administering an effective amount of a *Lactobacillus fermentum* LM1016 strain to the subject in need of preventing, ameliorating or treating cardiovascular diseases, obesity, diabetes mellitus or fatty liver disease.

Specifically, the *Lactobacillus fermentum* LM1016 strain has an effect of reducing inflammation in subcutaneous fat.

In addition, the *Lactobacillus fermentum* LM1016 strain has an effect of reducing the level of glucose, insulin or leptin in blood.

In addition, the *Lactobacillus fermentum* LM1016 strain reduces the weight of the liver or the amount of neutral fat in the liver, thereby having an effect of preventing or treating fatty liver disease.

The composition of the present invention may be used in a pharmaceutical product, a health functional food, a dairy product, a fermented product, a food additive or an animal feed.

Effect of the Invention

The *Lactobacillus fermentum* LM1016 strain of the present invention reduces CRP, neutral fat and cholesterol concentrations in blood, which are risk factors for cardiovascular diseases, thereby exhibiting an effect of preventing and treating cardiovascular diseases such as hypertension, hyperlipidemia and arteriosclerosis.

In addition, the novel LM1016 strain inhibits the accumulation of fat in the liver tissue, which is another cause of cardiovascular diseases, thereby having an effect of preventing and treating fatty liver.

In addition, the novel LM1016 strain has an effect of inhibiting the accumulation of body fat, reducing the size of fat cells, and inhibiting inflammatory response in fat cells, thereby having an effect of preventing and treating obesity and a disease caused by obesity.

In particular, the *Lactobacillus fermentum* LM1016 strain of the present invention rapidly reduces the blood glucose concentration and reduces the blood insulin concentration, thereby ameliorating insulin resistance and thus exhibiting an effect of preventing or treating diabetes mellitus, which may be a cause of cardiovascular diseases.

Therefore, the novel LM1016 strain of the present invention has an excellent effect of treating and preventing cardiovascular diseases, fatty liver, obesity and diabetes mellitus at the same time without side effects.

DETAILED DESCRIPTION FOR WORKING THE INVENTION

The present inventors have found a novel LM1016 strain of *Lactobacillus fermentum*.

In addition, the novel LM1016 strain reduces CRP, neutral fat and cholesterol concentrations in blood, which are risk factors for cardiovascular diseases, thereby having an effect of preventing and treating cardiovascular diseases such as hypertension, hyperlipidemia and arteriosclerosis.

In addition, the novel LM1016 strain inhibits the accumulation of fat in the liver tissue, which is another cause of cardiovascular diseases, thereby having an effect of preventing and treating fatty liver.

In addition, the novel LM1016 strain has an effect of inhibiting the accumulation of body fat, reducing the size of fat cells, and inhibiting inflammatory response in fat cells, thereby having an effect of preventing and treating obesity and a disease caused by obesity.

In particular, the *Lactobacillus fermentum* LM1016 strain of the present invention rapidly reduces the blood glucose concentration and reduces the blood insulin concentration, thereby ameliorating insulin resistance and thus exhibiting an effect of preventing or treating diabetes mellitus, which may be a cause of cardiovascular diseases.

Therefore, the novel LM1016 strain of the present invention has an excellent effect of treating and preventing cardiovascular diseases, fatty liver, obesity and diabetes mellitus at the same time without side effects, and as such, probiotics (*Lactobacillus fermentum*) having an effect of preventing and treating several chronic diseases at the same time have not been previously known.

Therefore, the present invention relates to a novel strain of *Lactobacillus fermentum* LM1016.

In addition, the present invention relates to a composition having an effect on cardiovascular diseases, fatty liver, obesity or diabetes mellitus, comprising a *Lactobacillus fermentum* LM1016.

The composition of the present invention may be used in a pharmaceutical product, a health functional food, a dairy product, a fermented product, a food additive or an animal feed or the like.

Specifically, the microorganism of the present invention may be administered in a unit form such as a tablet or capsule obtained by mixing with a carrier, excipient or diluent or the like selected according to the route of administration.

Carriers, excipients and diluents suitable for the composition of the present invention may include lactose, dextrose, sucrose, sorbitol, mannitol, starch, gum acacia, calcium phosphate, alginate, gum tragacanth, gelatin, calcium silicate, microcrystalline cellulose, polyvinylpyrrolidone, cellulose, syrup, methylcellulose, methyl and propyl hydroxybenzoate, talc, magnesium stearate or mineral oil or the like.

The "composition" in the present specification does not necessarily mean only approved as a pharmaceutical product, but is a concept including a general functional food or health supplement food.

As used herein, "cardiovascular illness" or "cardiovascular disease" refers to an illness affecting the heart and/or blood vessels. In particular, cardiovascular diseases include arrhythmia; arteriosclerosis; angina; dysrhythmia; myocardial ischemia; myocardial infarction; heart or vascular aneurysm; vasculitis; stroke; peripheral obstructive arteriopathy of a limb, organ or tissue; reperfusion injury due to ischemia of the brain, heart, kidney, or other organ or tissue; endotoxicity; surgical or traumatic shock; hypertension; valvular disease of heart; heart failure; abnormal blood pressure; shock; vasoconstriction; vascular abnormality, dysfunction limited to a single organ or tissue.

In another embodiment, the present invention provides a method for preventing, ameliorating or treating cardiovascular diseases, fatty liver, obesity or diabetes mellitus in a subject in need thereof, comprising administering an effective amount of a *Lactobacillus fermentum* LM1016 strain to the subject in need of preventing, ameliorating or treating cardiovascular diseases, fatty liver, obesity or diabetes mellitus.

As used herein, the term "subject" includes human and non-human animals. Non-human animals include all vertebrates, for example mammals and non-mammals, such as non-human primates, sheep, dogs, cattle, horses and the like.

In another embodiment, the present invention provides the use of a *Lactobacillus fermentum* LM1016 strain for preventing, ameliorating or treating cardiovascular diseases, fatty liver, obesity or diabetes mellitus.

Hereafter, the present invention will be described in more detail with reference to the following examples. It is intended that these examples illustrate the present invention in more detail and the scope of the present invention is not limited to these examples.

Example 1

Experiment of Inhibitory Action of LM1016 on Cardiovascular Disease Factor

In order to evaluate an influence of a *Lactobacillus fermentum* LM1016 strain deposited with the Korean Culture Center of Microorganisms, the Korea Research Institute of Bioscience and Biotechnology, under accession number KCCM12468P on cardiovascular disease factor, 5 week-old C57BL6/J mice were tamed for 1 week and then were divided into 3 groups, and the experiment was conducted.

Group 1 was a group that was administered with a normal diet (ND, 3.1 kcal/g) for 12 weeks, Group 2 was a group that was administered with ND for the first 2 weeks and with a high fat diet (HFD, 5.2 kcal/g) for remaining 10 weeks, and Group 3 was a group that was orally administered with LM1016 ($10^9$ CFU/mouse) 5 times a week for 12 weeks while being administered with the same diet as in Group 2.

After the 12-week administration was completed, blood was collected from the heart of mice, and the CRP concentration, neutral fat and cholesterol concentration in the blood were measured. The results are shown in Table 1 below and FIG. 1.

TABLE 1

Figure 1:
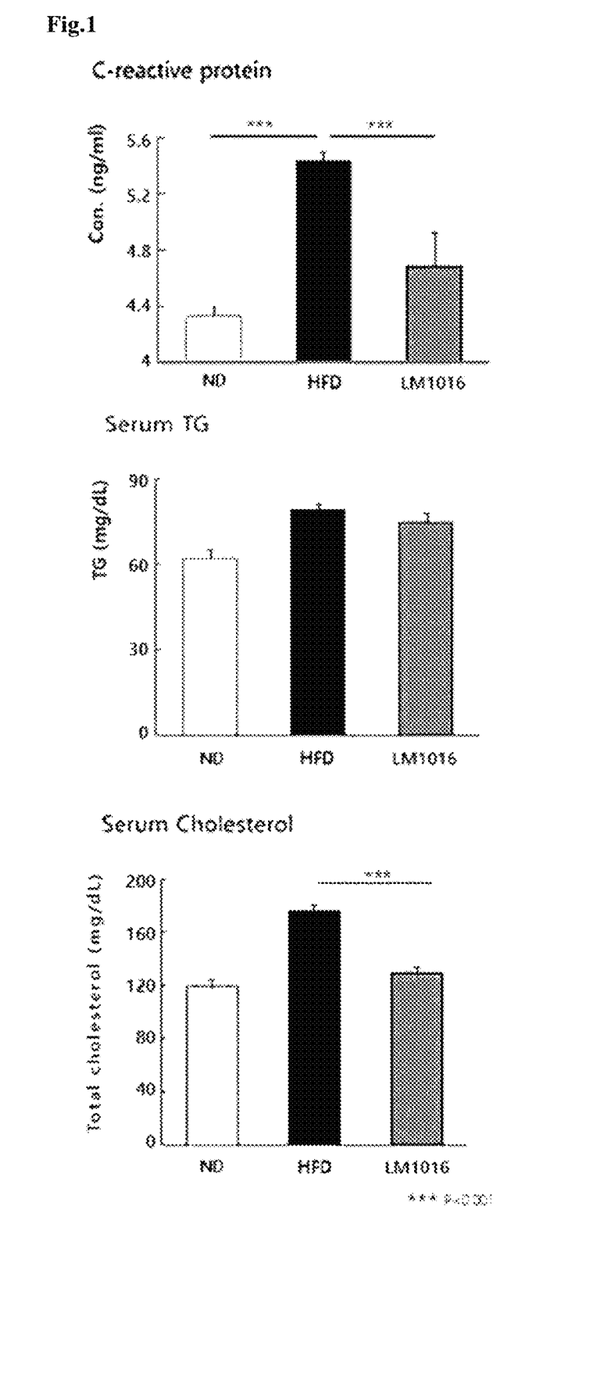
FIG. 1 shows the levels of C-reactive protein, neutral fat, and total cholesterol in the serum of mice of Groups 1 to 3.

|  | Group 1 | Group 2 | Group 3 |
| --- | --- | --- | --- |
| CRP (ng/ml) | 4.3 | 5.4 | 4.6 |
| Neutral fat (mg/dL) | 62.0 | 79.0 | 74.9 |
| Total cholesterol (mg/dL) | 119.4 | 176.0 | 129.3 |

As shown in Table 1 above, it was confirmed that the CRP concentration in the blood was remarkably reduced to 4.6 ng/ml in Group 3 administered with LM1016 as compared with 5.4 ng/mg in Group 2, which was similar level to Group 1 (4.33 ng/ml) administered with a normal diet.

In addition, the concentration of neutral fat in the blood was 62.0 mg/dL in Group 1, 79.0 mg/dL in Group 2, and 74.9 mg/dL in Group 3, and there was no significant difference in levels between Group 2 and Group 3. However, the total cholesterol concentration was 176.0 mg/dL in Group 2 and 129.3 mg/dL in Group 3, and it was confirmed that the total cholesterol concentration of Group 3 was lowered by 46.7 mg/dL as compared with that of Group 2 and was similar level to that of Group 1.

In the end, it can be seen that the *Lactobacillus fermentum* LM1016 strain has an excellent effect of restoring to normal level by reducing the CRP concentration and the total cholesterol concentration.

Example 2

Inhibitory Effect of LM1016 on Body Weight Gain Rate, Accumulation of Body Fat and Inflammatory Response The body weight was measured weekly while conducting the animal experiment for cardiovascular diseases of Example 1. At week 12, the mice were anatomized, and each of the main organs was extracted, and the weight thereof was measured.

1. Reduction of Body Weight Gain Rate

The cumulative amount of body weight gain over time was measured based on the body weight at week 0, and is shown in Table 2 below and FIG. 2.

Figure 2:
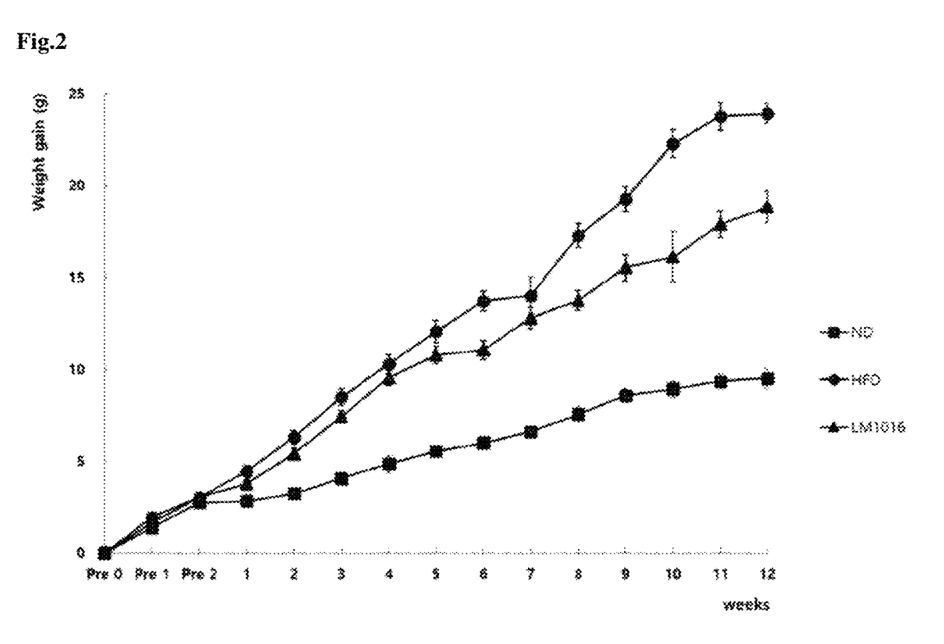
FIG. 2 shows the change in the cumulative amount of body weight gain of Groups 1 to 3.

As shown in FIG. 2, the amount of body weight gain for 2 weeks before administration of the high fat diet showed a gentle cumulative increase in all three groups. In Group 2 and Group 3, as the high-fat diet was administered, the difference in the amount of body weight gain gradually began to appear and showed a distinct difference from week 5.

TABLE 2

|  | Group 1 | Group 2 | Group 3 |
| --- | --- | --- | --- |
| Amount of body weight gain at week 11 (g) | 9.35 | 23.77 | 17.89 |
| Amount of body weight gain at week 12 (g) | 9.50 | 23.92 | 18.84 |

As shown in Table 2 above, it was confirmed that at week 11, the amount of body weight gain of Group 2 was 23.77 g, and the amount of body weight gain of Group 3 was 17.89 g, and the amount of body weight gain of Group 3 was reduced by 5.88 g as compared with that of Group 2.

At week 12, it was confirmed that the amount of body weight gain of Group 2 was 23.92 g, and the amount of body weight gain of Group 3 was 18.84 g, and the amount of body weight gain of Group 3 was reduced by 5.08 g as compared with that of Group 2, and thus, the body weight gain rate of Group 3 was reduced by 17% or more as compared with that of Group 2.

In the end, as a result of comparing Group 2 administered with the high fat diet and Group 3 administered with the high fat diet in combination with LM1016 at the same time, it can be seen that the difference in the body weight gain rate was shown since week 1, and the difference in the body weight gain rate was remarkably increased over time. Therefore, it can be seen that LM1016 has an effect of reducing body weight.

2. Reduction of Subcutaneous Fat, Epididymal Fat, and Brown Adipose Tissue

Figure 3:
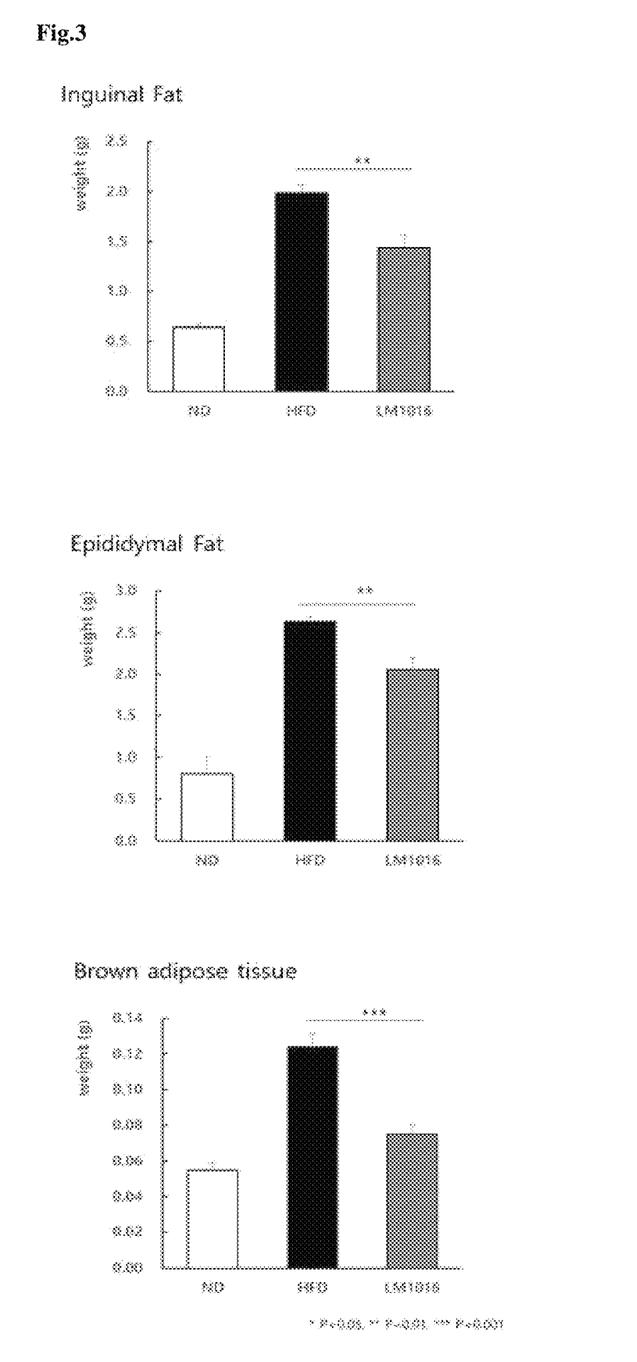
FIG. 3 shows the amount of subcutaneous fat, epididymal fat, and brown fat in mice of Groups 1 to 3.
Figure 4:
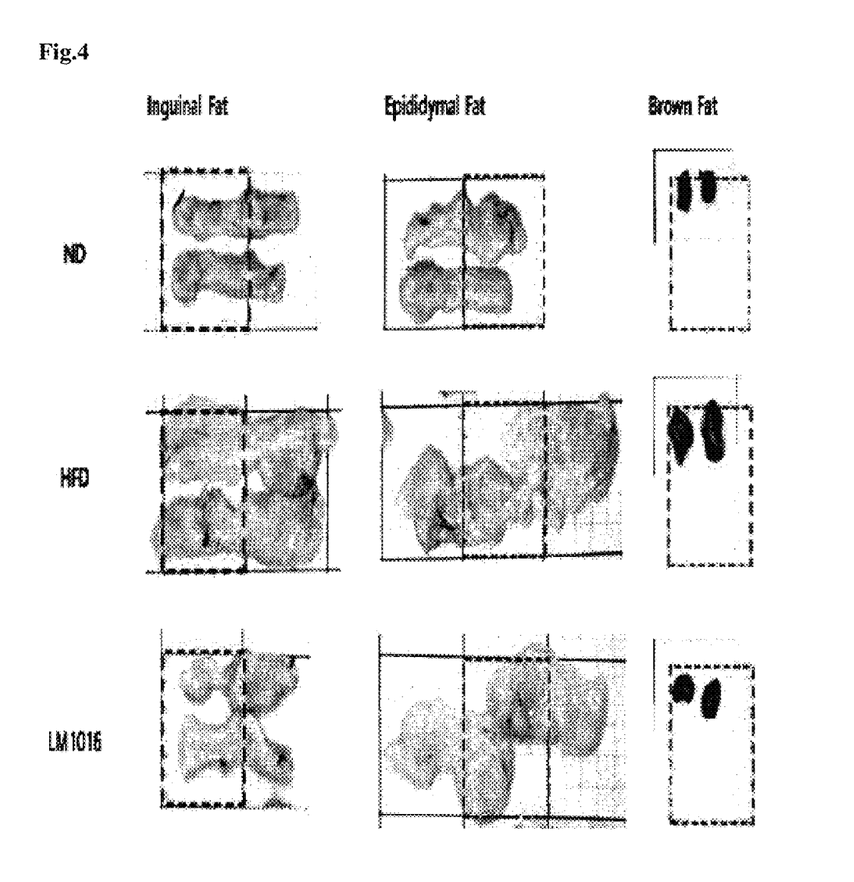
FIG. 4 shows the size of subcutaneous fat, epididymal fat, and brown fat in mice.

The weights of subcutaneous fat, epididymal fat, and brown adipose tissue for 12 weeks were measured, and the results are shown in Table 3 below, and FIGS. 3 and 4.

TABLE 3

|  | Group 1 | Group 2 | Group 3 |
| --- | --- | --- | --- |
| Subcutaneous fat (g) | 0.64 | 1.99 | 1.44 |
| Epididymal fat (g) | 0.80 | 2.63 | 2.05 |
| Brown adipose tissue (g) | 0.06 | 0.12 | 0.08 |

As shown in Table 3 above, it was confirmed that the increased amount of all subcutaneous fat, epididymal fat, and brown adipose tissue of Group 3 administered with the high fat diet in combination with LM1016 was reduced as compared with that of Group 2 administered with the high fat diet.

Figure 5:
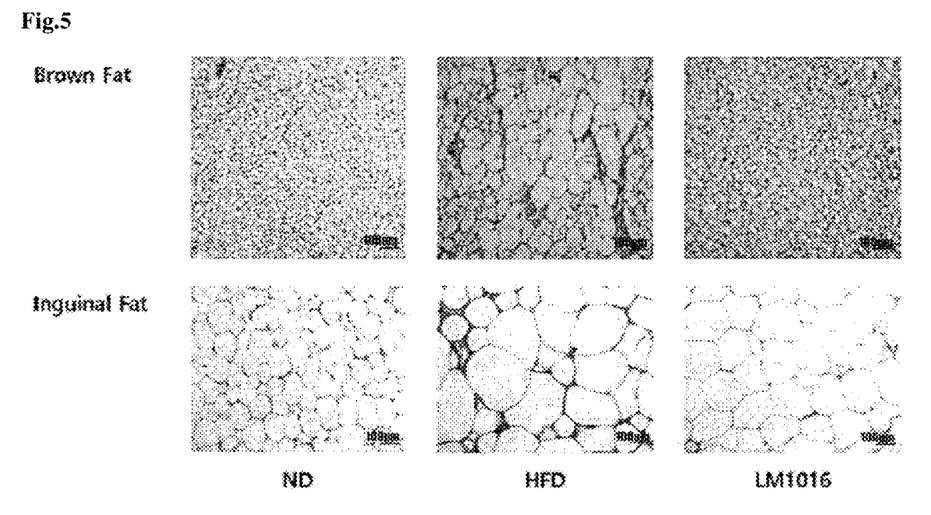
FIG. 5 shows the number of adipose tissue and the size of fat cells by staining with H&E stain in epididymal fat and brown fat in each group.

In addition, the epididymal fat was stained with H&E stain, and the results are shown in FIG. 5. As shown in FIG. 5, it was confirmed that the size of the fat cells of Group 2 was the largest, and the size of the fat cells of Group 3 was reduced to less than half as compared with that of Group 2.

The size of the fat globule was measured, and the results are shown in Table 4 below.

TABLE 4

| | Group 1 | Group 2 | Group 3 |
|---|---|---|---|
| Size of fat globule of subcutaneous fat ($\mu m^2$) | 15,896 | 62,114 | 35,652 |

As shown in Table 4 above, the size of the fat globule of Group 1 was 15,896 $\mu m^2$, that of Group 2 was 62,114 $\mu m^2$, and that of Group 3 was 35,652 $\mu m^2$.

3. Reduction of Inflammatory Response in Subcutaneous Fat

Figure 6:
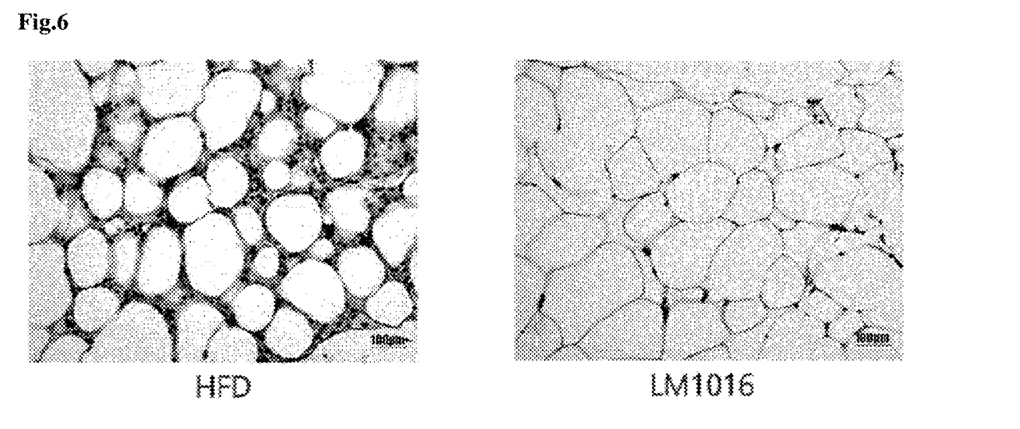
FIG. 6 shows the shape of the fat and the inflammatory response between the cells by treating epididymal fat of Group 2 and Group 3 by immunochemical staining.

The inflammatory response in subcutaneous fat was confirmed by immunochemical staining using the F4/80 antibody. As a result, as shown in FIG. 6, it was confirmed that the shape of the cells of the subcutaneous fat of the mice administered with the high fat diet was distorted, and a blue spot that appeared to be inflammation between these cells was confirmed, but in the group administered with LM1016, the cell shape was maintained clean, and almost no inflammatory response occurred.

Example 3

Antidiabetic Effect of LM1016
1. Reduction of Blood Sugar

Figure 7:
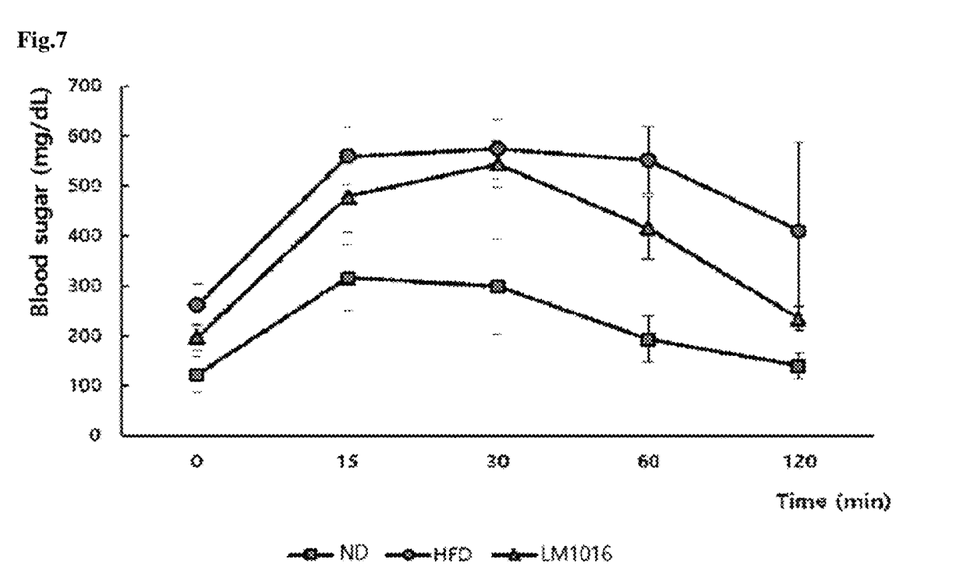
FIG. 7 shows the blood glucose level in mice of Groups 1 to 3.

In order to measure the glucose tolerance of the mice, glucose was administered 11 weeks after the start of administration to each group, and then the change in blood sugar over time was measured, and the results are shown in Table 5 and FIG. 7.

TABLE 5

| Time (min) | Group 1 Blood sugar (mg/dL) | Group 2 Blood sugar (mg/dL) | Group 3 Blood sugar (mg/dL) |
|---|---|---|---|
| 0 | 122.83 | 262.50 | 197.50 |
| 15 | 316.33 | 559.83 | 478.83 |
| 30 | 299.00 | 575.17 | 544.83 |
| 60 | 193.50 | 552.17 | 415.67 |
| 120 | 140.00 | 410.67 | 234.67 |

As shown in Table 5 above, it was confirmed that the blood sugar level in Group 2 administered with the high fat diet was the highest from the initial administration to 120 minutes. On the other hand, the blood sugar level in Group 3 administered with the high fat diet in combination with LM1016 was increased during the initial 30 minutes, but the blood sugar level of Group 3 was lower than the blood sugar level of Group 2.

In addition, it was confirmed that from 30 minutes after administration, the blood sugar of Group 3 was reduced sharply, and after 120 minutes, the blood sugar of Group 3 was reduced to a level similar to that of Group 1.

Therefore, it can be seen that LM1016 has an effect of reducing the glucose tolerance due to a high fat diet by reducing the blood sugar.

2. Reduction of Levels of Insulin and Leptin

Figure 8:
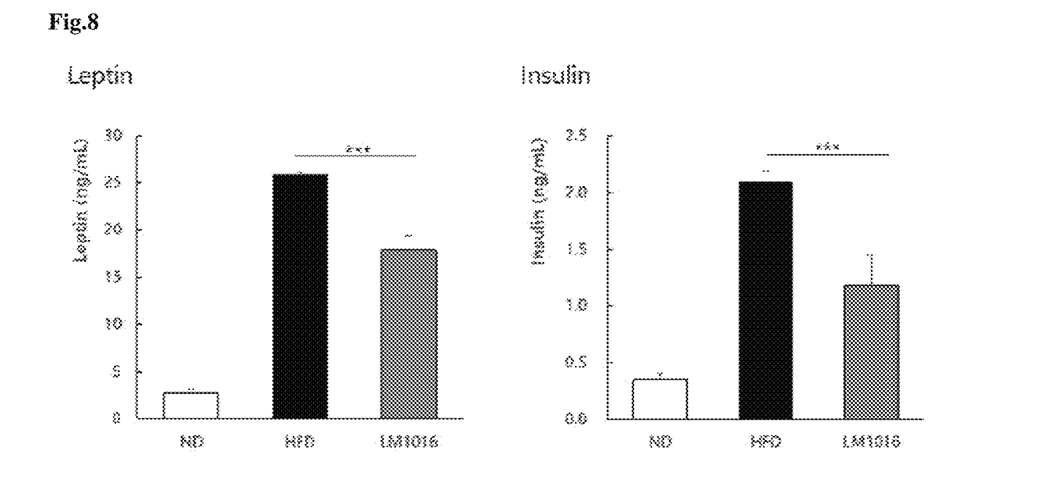
FIG. 8 shows the levels of leptin and insulin in serum.

The levels of insulin and leptin in each group for 12 weeks were measured, and the results are shown in Table 6 below and FIG. 8.

TABLE 6

| | Group 1 | Group 2 | Group 3 |
|---|---|---|---|
| Insulin (ng/mL) | 0.36 | 2.09 | 1.19 |
| Leptin (ng/mL) | 2.73 | 25.78 | 17.92 |

As shown in Table 6 above, it was confirmed that the insulin level of Group 3 was remarkably reduced to about half of the insulin level of Group 2.

In the case of obesity, the insulin resistance is increased, resulting in the increase of the insulin secretion. It can be seen that LM1016 has an effect of reducing the insulin resistance due to a high fat diet by reducing the insulin concentration.

In addition, the leptin level of Group 2 was 25.78 ng/mL, and the leptin level of Group 3 was 17.92 ng/mL. It was found that the leptin level of Group 3 was remarkably reduced as compared with the leptin level of Group 2.

Leptin is an appetite-regulating hormone secreted from fat cells. When neutral fats accumulate in adipose tissue and the size of fat cells increases, the synthesis of leptin is promoted and the concentration of leptin increases. Therefore, it can be seen that the concentration of leptin of Group 3 is remarkably reduced as compared with that of Group 2 because neutral fats and fat cells are reduced due to the administration of LM1016.

Example 4

Effect of Ameliorating Fatty Liver
1. Weight of Liver and Amount of Neutral Fat in Liver After 12 weeks of administration, the liver of mice was extracted in each group, and the weight of the liver and the amount of neutral fat in the liver tissue were measured, and the results are shown in Table 7 below and FIG. 9.

TABLE 7

Figure 9:
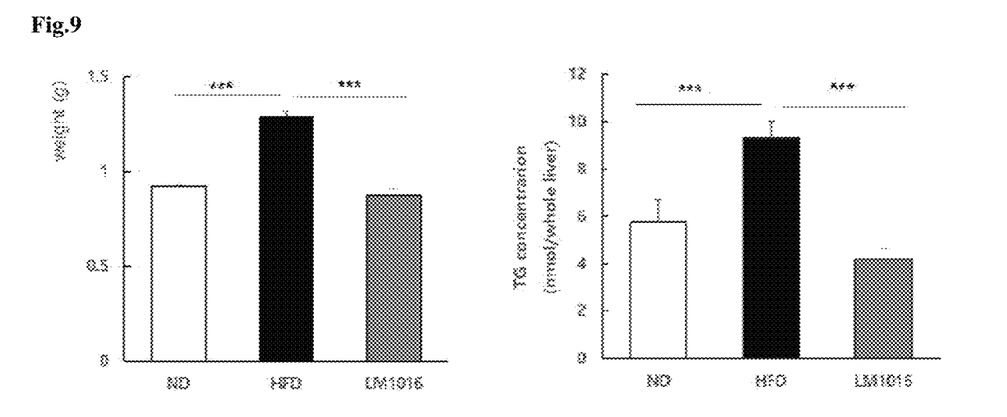
FIG. 9 shows the weight of the liver and the amount of neutral fat in the liver.

| | Group 1 | Group 2 | Group 3 |
|---|---|---|---|
| Weight of liver (g) | 0.92 | 1.29 | 0.88 |
| Amount of neutral fat (nmol/whole liver) | 5.78 | 9.33 | 4.20 |

As shown in Table 7 above, it was confirmed that the weight of the liver of Group 3 was remarkably reduced as compared with that of Group 2, and it was also reduced as compared with that of Group 1.

In addition, as a result of measuring the amount of neutral fat in the liver tissue, it was found that the amount of neutral fat in the liver tissue of Group 2 was 9.33 nmol/whole liver, and that of Group 3 was 4.20 nmol/whole liver. It can be seen that the amount of neutral fat of Group 3 was remarkably reduced to less than half of that of Group 2. In addition, the amount of neutral fat of Group 2 was lower than that of Group 1.

Therefore, fat metabolism in the body occurs abnormally as the person becomes overweight, and lipid substances are accumulated in the liver, resulting in an increase in the weight of the liver and the amount of neutral fat in the liver tissue. Thus, it can be seen that the LM1016 strain is involved in lipid metabolism in the liver and has an effect of inhibiting the accumulation of fats in the hepatocytes.

2. Reduction of Fatty Liver

Figure 10:
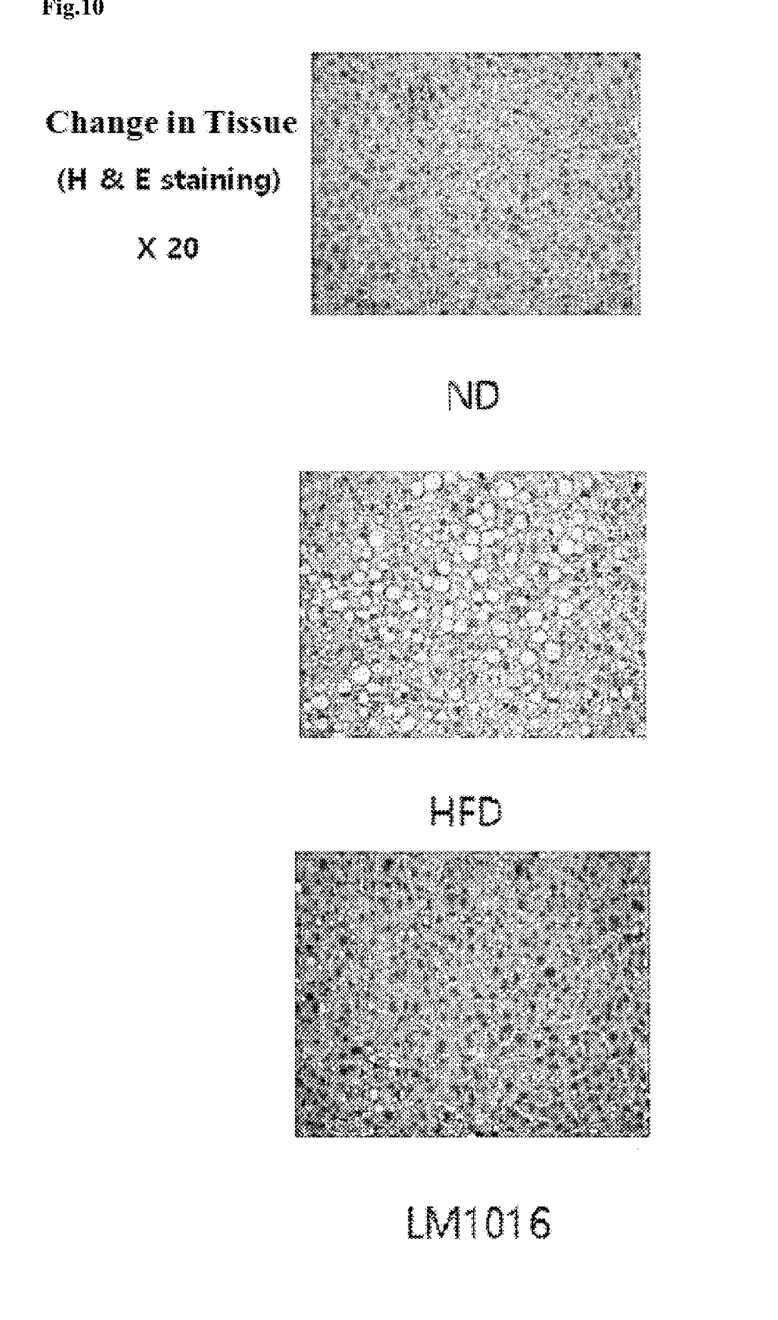
FIG. 10 shows the results of observing the presence or absence of fatty liver by staining liver tissue with H&E stain.

The liver was stained with H&E stain, and the presence or absence of a macro fat vacuole (×20 magnifications and ×40 magnifications) was observed and is shown in FIG. 10.

As shown in FIG. 10, the liver tissues of Group 1 and Group 3 were densely packed, but white portions, which appear to be macro fat vacuoles, were observed throughout the liver tissues of Group 2. Therefore, it can be seen that the LM1016 strain has an excellent effect of inhibiting fatty liver.

The invention claimed is:

1. A *Lactobacillus fermentum* LM1016 strain (KCCM12468P).

2. A pharmaceutical composition for preventing or treating cardiovascular diseases, comprising a *Lactobacillus fermentum* LM1016 strain (KCCM12468P).

3. The pharmaceutical composition according to claim 2, wherein the *Lactobacillus fermentum* LM1016 strain (KCCM12468P) reduces the level of CRP (C-reactive protein), neutral fat or cholesterol, which is a risk factor for cardiovascular diseases.

4. The pharmaceutical composition according to claim 2, wherein the composition has an additional effect of preventing or treating obesity, diabetes mellitus or fatty liver disease.

5. The pharmaceutical composition according to claim 4, wherein the *Lactobacillus fermentum* LM1016 strain (KCCM12468P) reduces inflammation in subcutaneous fat.

6. The pharmaceutical composition according to claim 4, wherein the *Lactobacillus fermentum* LM1016 strain (KCCM12468P) reduces the level of glucose, insulin or leptin in blood.

7. The pharmaceutical composition according to claim 4, wherein the *Lactobacillus fermentum* LM1016 strain (KCCM12468P) reduces the weight of the liver or the amount of neutral fat in the liver.

8. A food composition for preventing or ameliorating cardiovascular diseases, comprising a *Lactobacillus fermentum* LM1016 strain (KCCM12468P).

9. The food composition for preventing or ameliorating cardiovascular diseases according to claim 8, wherein the food composition is a health functional food, a dairy product, a fermented product or a food additive.

10. An animal feed composition for preventing or ameliorating cardiovascular diseases, comprising the *Lactobacillus fermentum* LM1016 strain (KCCM12468P) according to claim 1.

* * * * *